United States Patent [19]
Seibel et al.

[11] Patent Number: 5,836,959
[45] Date of Patent: Nov. 17, 1998

[54] ULTRASONIC TIP AND A METHOD FOR INTEROCULAR SURGERY

[76] Inventors: Barry S. Seibel, 11756 Kiowa Ave. #203, Los Angeles, Calif. 90049; Alex Urich, 27402 Via Caudaloso, Mission Viejo, Calif. 92692

[21] Appl. No.: 631,007

[22] Filed: Apr. 12, 1996

[51] Int. Cl.⁶ .................................................. A61B 17/32
[52] U.S. Cl. .......................... 606/169; 606/167; 606/170; 606/180; 604/22
[58] Field of Search .................................... 606/169, 167, 606/170, 180; 604/22

[56] References Cited

U.S. PATENT DOCUMENTS

| | | | |
|---|---|---|---|
| 4,838,853 | 6/1989 | Parisi | 606/169 |
| 5,188,102 | 2/1993 | Idemoto et al. | 606/169 |
| 5,324,299 | 6/1994 | Davison et al. | 606/169 |
| 5,413,578 | 5/1995 | Zahedi | 606/169 |

*Primary Examiner*—Michael Powell Buiz
*Assistant Examiner*—Daphna Shai
*Attorney, Agent, or Firm*—Blakely Sokoloff Taylor & Zafman

[57] ABSTRACT

An ultrasonically driven phaco tip and an interocular procedure for emulsifying a lense of an eye. The tip includes a flat distal end which has a pair of adjacent shoulders. The flat end creates a more efficient cutting surface. The shoulders provide a relatively large surface area that focuses ultrasonic pressure waves into the bubbles of an irrigation fluid that surrounds the tip. The focused pressure waves induce cavitation within the fluid and emulsification of the lense tissue. A lense may be emulsified by inserting the phaco tip into the anterior chamber of an eye and sculpting a bowl in the center of the lense. The tip is then rotated to a vertical position and used to cut a groove in the lense. The groove may be widen by another pass of the phaco tip so that the tip and a splitting instrument can be inserted into the widen groove. The tip and instrument are then pulled in opposite directions to crack the lense. Alternatively, the lense can be cracked by merely rotating the phaco tip while the tip is within the groove. The process of cutting grooves and cracking the lense is repeated to create a number of small lense fragments. The tip is then rotated to a horizontal position to emulsify and aspirate the lense tissue.

5 Claims, 4 Drawing Sheets

ULTRASONIC TIP AND A METHOD FOR INTEROCULAR SURGERY

BACKGROUND OF THE INVENTION

1. Field of the Invention

The present invention relates to an apparatus and procedure for emulsifying a lense located within the anterior chamber of an eye.

2. Description of Related Art

Cataracteous lenses are typically removed in an interocular procedure using an ultrasonically driven surgical instrument. The instrument has a phaco tip that is inserted into the anterior chamber of the eye to emulsify the lense. The tip is coupled to an irrigation fluid and an aspiration line to aspirate the emulsified lense.

Conventional phaco tips are typically constructed from a small cylindrical tube which has a cutting edge located at the distal end of the tip. Coupled to the tip is an outer sleeve which has an irrigation port that introduces irrigation fluid to the working area of the lense. Phaco tips also have a central aspiration opening that allows the emulsified lense tissue to be drawn out of the eye.

The tip is driven in a linear oscillating motion to enhance the cutting action of the lense. The rapid movement of the tip is similar to the movement of a saw and is quite effective in cutting the lense tissue. The oscillatory movement of the tip also induces a cavitation effect in the fluid adjacent to the working surface of the lense. Cavitation is the formation of cavities created by the collapse of air bubbles within a fluid medium. The collapsing bubbles create instantaneous temperatures and pressures of approximately 5000° C. and 10,000 psi, respectively. The pressures and temperatures created by millions of collapsing bubbles further emulsify the lense tissue.

The number and size of bubbles that collapse is proportional to the ultrasonic energy transferred to the bubbles from the oscillating tip. It is desirable to provide a phaco tip that can radiate focused ultrasonic pressure waves to the bubbles. The round end of a conventional cylindrical phaco tip does not generate focused ultrasonic pressure. Consequently, cylindrical tips are relatively inefficient in creating cavitation within the irrigation fluid. It would be desirable to provide a phaco tip that induces a higher level of cavitation than tips of the prior art.

There have been developed various techniques for emulsifying the lense of an eye. FIGS. 1–3 show a quadrant procedure where the tip 2 cuts two intersecting grooves 4 across the lense 6. The lense 6 is then cracked into four quadrant fragments. The four pieces are then emulsified and aspirated out of the eye. Cutting across to edge of the lense 6 creates a risk of damaging the anterior capsular rim 8, particularly for small to medium size pupils.

FIGS. 4 and 5 show a procedure known as phaco chop. In a phaco chop procedure a small bowl 10 is initially sculpted from the center of the lense 6 and a splitting instrument 12 is embedded into the lense material. The tip 2 is manipulated to cut toward the instrument 12 and induce a crack 14 in the lense 6. The process is repeated to create a number of lense fragments. The fragments are then emulsified and aspirated from the anterior chamber. The phaco chop procedure also poses a potential risk of damaging the anterior capsular rim. Additionally, it has been found that cylindrical shaped phaco tips tend to core into the lense material. Coring is a relatively inefficient means of cutting, and may also create occlusions in the aspiration line of the system. It would be desirable to provide a tip and a procedure that is faster and has a higher level of safety than tips and procedures of the prior art.

SUMMARY OF THE INVENTION

The present invention is an ultrasonically driven phaco tip and an interocular procedure for emulsifying a lense of an eye. The tip includes a flat distal end which has a pair of adjacent shoulders. The flat end creates a more efficient cutting surface. The shoulders provide a relatively large surface area that focuses ultrasonic pressure waves into the bubbles of an irrigation fluid that surrounds the tip. The focused pressure waves induce cavitation within the fluid and emulsification of the lense tissue. A lense may be emulsified by inserting the phaco tip into the anterior chamber of an eye and sculpting a bowl in the center of the lense. The tip is then rotated to a vertical position and used to cut a groove in the lense. The groove may be widen by another pass of the phaco tip so that the tip and a splitting instrument can be inserted into the widen groove. The tip and instrument are then pulled in opposite directions to crack the lense. Alternatively, the lense can be cracked by merely rotating the phaco tip while the tip is within the groove. The process of cutting grooves and cracking the lense is repeated to create a number of small lense fragments. The tip is then rotated to a horizontal position to emulsify and aspirate the lense tissue.

BRIEF DESCRIPTION OF THE DRAWINGS

The objects and advantages of the present invention will become more readily apparent to those ordinarily skilled in the art after reviewing the following detailed description and accompanying drawings, wherein.

DETAILED DESCRIPTION OF THE INVENTION

Figure 1:
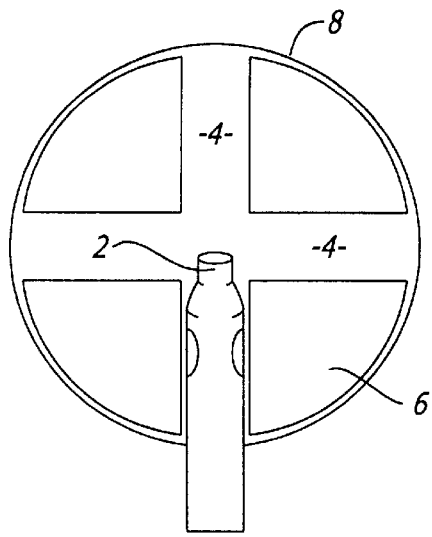
FIG. 1 is a schematic top view showing a tip that cuts four grooves in a lense in a procedure of the prior art.
Figure 2:
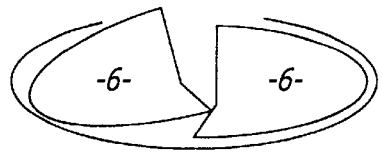
FIG. 2 is a schematic side view showing the lense of FIG. 1 being cracked.
Figure 3:
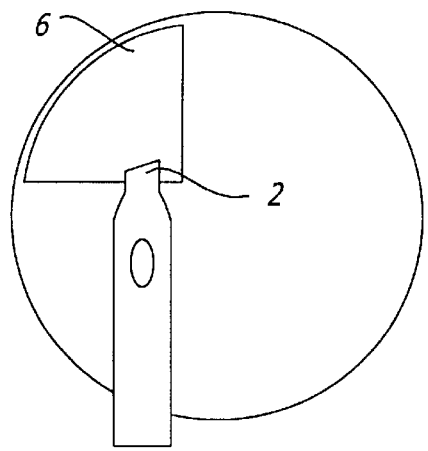
FIG. 3 is a schematic top view showing the lense of FIG. 1 being emulsified.
Figure 4:
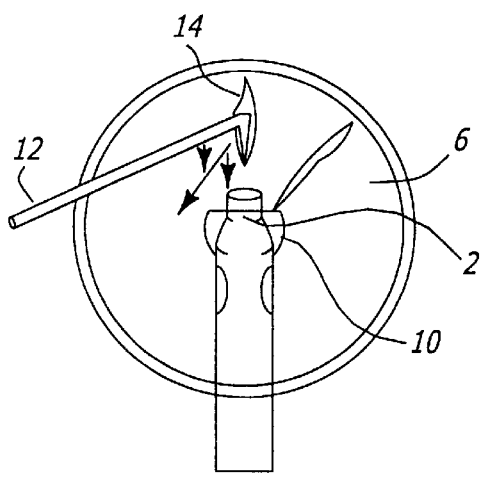
FIG. 4 is a schematic top view showing a tip and a splitting instrument inducing a crack in a lense in a procedure of the prior art.
Figure 5:
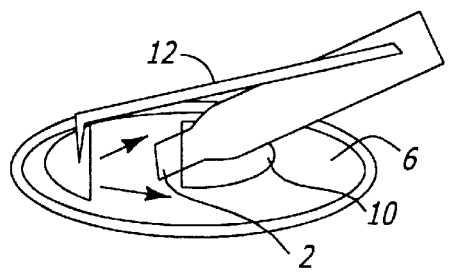
FIG. 5 is a schematic side view showing the lense of FIG. 4 being cracked.
Figure 6:
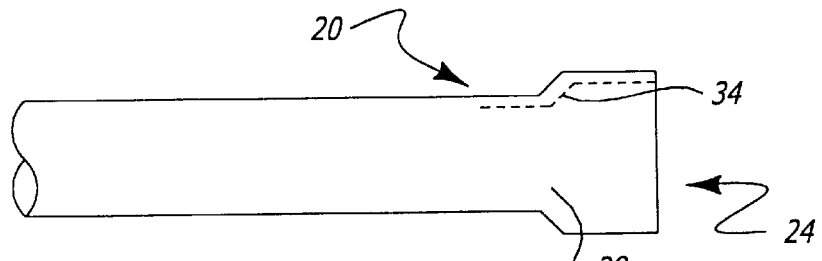
FIG. 6 is a top view of a phaco tip of the present invention.
Figure 7:
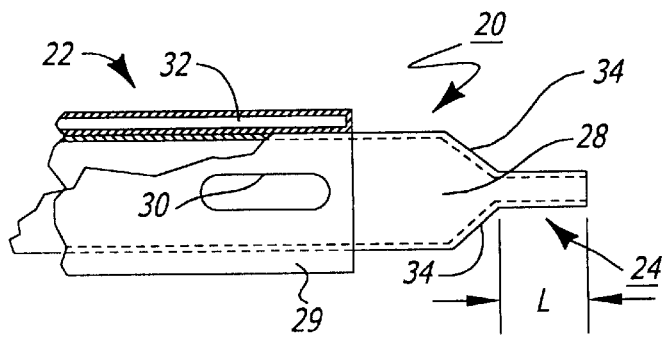
FIG. 7 is a side view of the phaco tip.
Figure 8:
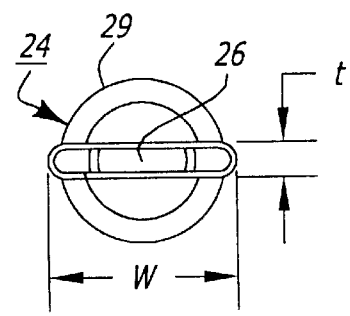
FIG. 8 is an end view of the phaco tip.

Referring to the drawings more particularly by reference numbers, FIGS. 6–8 show a phaco tip 20 of the present invention. The tip 20 has a proximal end 22 and a flat distal end 24. The distal end 24 has an opening 26 that provides fluid communication between the tip ambient and an aspiration channel 28 that extends through the length of the tip 20. Coupled to the tip 20 is an outer sleeve 29 which has an irrigation port 30 that is coupled to a corresponding irrigation channel 32.

The flat distal end 24 has a width W that is typically larger than the diameter of the tip 20. The longer width W increases the cutting edge of the distal end and the cutting efficiency of the tip 20. Located at the base of the distal end 24 are a pair of shoulders 34. The shoulders 34 increase the effective area of the tip end and improve fluid cavitation induced by the tip 20. The flat distal portion also creates inner shoulders 34 within the aspiration channel 28 of the tip 20. The inner shoulders 34 also induce cavitation within a working fluid.

The tip 20 is preferably constructed by crimping the end of a cylindrical phaco tip. In the preferred embodiment, the length L of the distal end 24 is between 0.1 and 0.5 centimeters (cm). The width W of the distal tube 24 is between 0.1 and 0.2 cm, and the thickness t ranges from 0.05 to 0.09 cm. The diameter of the tip tube is preferably between 0.09 and 0.15 cm. The tip 20 is typically constructed from a titanium or stainless steel material.

Figure 9:
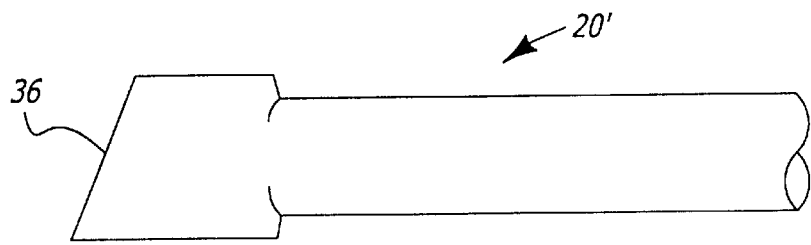
FIG. 9 is a top view of an alternate embodiment of the phaco tip.
Figure 10:
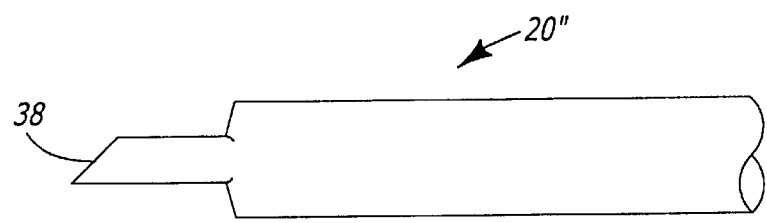
FIG. 10 is a side view of an alternate embodiment of the phaco tip.

FIG. 9 shows an alternate embodiment of a phaco tip 20' which has an oblique cutting edge 36 that extends along the width of the distal end 24. FIG. 10 is an alternate embodiment of a phaco tip 20" which has an oblique cutting edge 38 that extends along the thickness of the distal end 24. The angles of the cutting edges may vary between 0 and 45 degrees. The oblique cutting edges 36 and 38 may improve the cutting performance of the tip. Although separate oblique cutting edges are shown and described, it is to be understood that one tip may have both types of oblique cutting edges.

Figure 11:
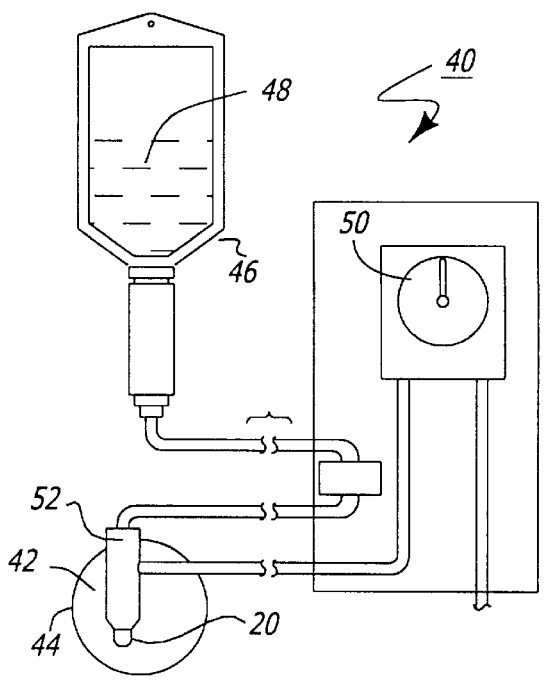
FIG. 11 a is schematic showing the phaco tip incorporated into a phaco system.

FIG. 11 shows the phaco tip 20 incorporated in a phaco system 40 and inserted into the anterior chamber 42 of an eye 44. The system 40 includes an irrigation bag 46 that is filled with irrigation fluid 48 and coupled to the irrigation channel 32 of the sleeve 29. The irrigation bag 46 is typically located at an elevation above the phaco tip 20 so that the irrigation fluid 48 flows into the eye under gravitational forces.

The system 40 also contains a pump 50 that is coupled to the aspiration line 28 of the tip 20. The pump 50 is typically of the peristaltic type which can create a negative pressure within the aspiration line 28. The pump 50 is typically coupled to a foot pedal (not shown) which allows the surgeon to control the vacuum pressure within the line 28.

The phaco tip 20 is located at the end of a handle 52 that can oscillate the tip 20 at an ultrasonic frequency. The ultrasonic transducer (not shown) within the handle 52 can be controlled by the surgeon through an input device (not shown).

Figure 12:
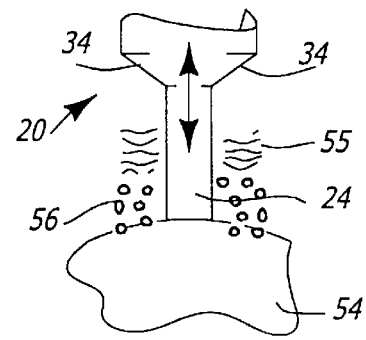
FIG. 12 is a schematic side view showing the tip cutting a lense.
Figure 13:
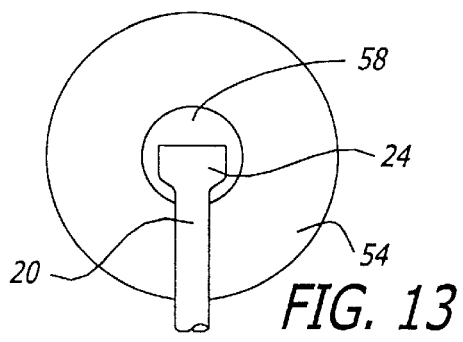
FIG. 13 is a schematic top view showing the tip sculpting a bowl into the center of a lense.
Figure 14:
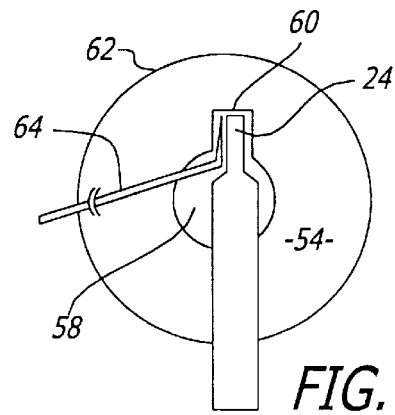
FIG. 14 is a schematic top view showing the tip and a splitting instrument within a groove of the lense.
Figure 15:
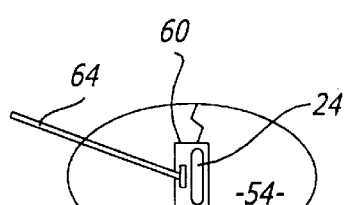
FIG. 15 is a schematic side view of FIG. 14.

As shown in FIG. 12, the system 40 is used to emulsify and aspirate a lense 54 of the eye 44. The lense 54 is emulsified by placing the ultrasonically driven tip 20 into contact with the lense tissue. The oscillatory movement of the tip creates a saw-like cutting effect on the lense tissue. The longer width of the flat distal end 24 increases the cutting area of the edge and the cutting performance of the tip 20.

The oscillatory movement of the tip 20 also creates pressure waves 55 that are transmitted to bubbles 56 trapped in the irrigation fluid 48. The pressure waves 55 cause the bubbles 56 to collapse and induce cavitation within the fluid. The collapsing bubbles create very high pressures and temperatures that further emulsify the tissue.

The shoulders 34 are in close proximity to the cutting edge and increase the effective working area of the tip 20. The larger effective working area increases the pressure of the waves that induce cavitation of the bubbles. Additionally, the shoulders 34 focus the pressure waves to further improve the cavitational efficiency of the tip 20. The cutting and cavitational effects of the tip 20 have been found to be relatively effective in emulsifying tissue. The emulsified tissue is aspirated from the eye through the aspiration channel 28.

FIGS. 13–18 show a phaco tip 20 used in a procedure to emulsify a lense 54. The tip 20 is initially inserted into the anterior chamber 42 through an incision in the eye. The tip 20 is oriented in a position so that the flat portion of the distal end 24 is essentially parallel with the lense (horizontal position). The ultrasonically tip 20 is then manipulated by the surgeon to create a bowl 58 in the center of the lense 54. The bowl is typically 3.5 millimeters (mm) wide and 3.5 mm deep.

The tip 20 is rotated so that the flat portion is essentially perpendicular to the lense 54 (vertical position). Starting from the bowl the tip 20 is manipulated to cut a groove 60 in the lense 54. The groove 60 is widened by a second pass of the tip 20. The groove 60 is preferably not cut to the edge of the lense 54 to avoid any possible cutting of the anterior capular rim 62.

Figure 16:
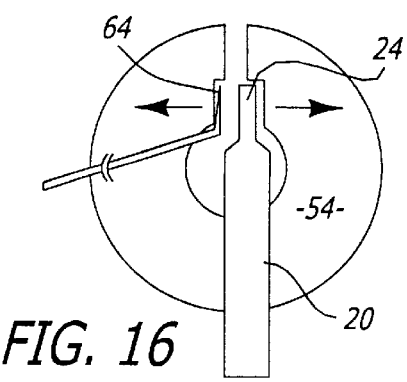
FIG. 16 is a schematic top view showing the tip and instrument being pulled to crack the lense.
Figure 17:
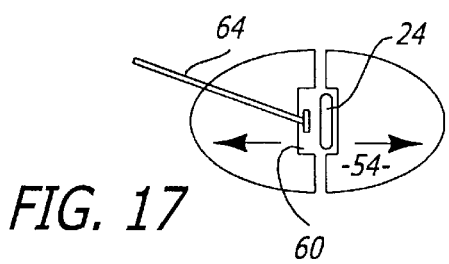
FIG. 17 is a schematic side view of FIG. 16.

The tip 20 and a surgical instrument 64 are inserted into the groove 60. As shown in FIGS. 16 and 17, the surgeon pulls on the tip 20 and instrument 64 in opposite directions to crack the lense 54. The lense 54 is rotated by the splitting instrument 64 and the process of cutting grooves and splitting the lense is repeated to create a number of lense fragments. The grooves 60 are formed with a relatively low aspiration pressure to insure that the capsular rim 62 is not drawn into the tip 20.

Figure 18:
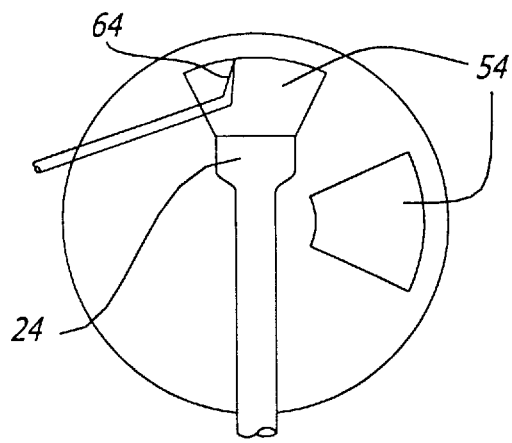
FIG. 18 is a schematic top view showing a rotated tip emulsifying lense fragments.

As shown in FIG. 18, the tip 20 is rotated to the horizontal position. The vacuum pressure is increased and the lense fragments 54 are emulsified and aspirated by feeding the fragments into the ultrasonically driven tip with the surgical instrument 64.

Figure 19:
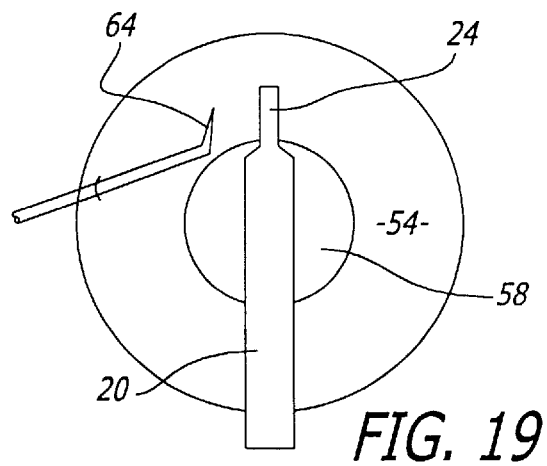
FIG. 19 is a schematic top view showing the tip embedded into a groove of the lense.
Figure 20:
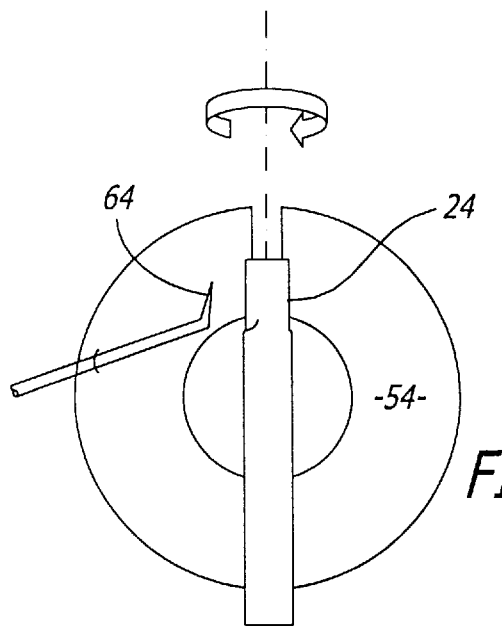
FIG. 20 is a schematic top view showing the tip being rotated within the groove to crack the lense.
Figure 21:
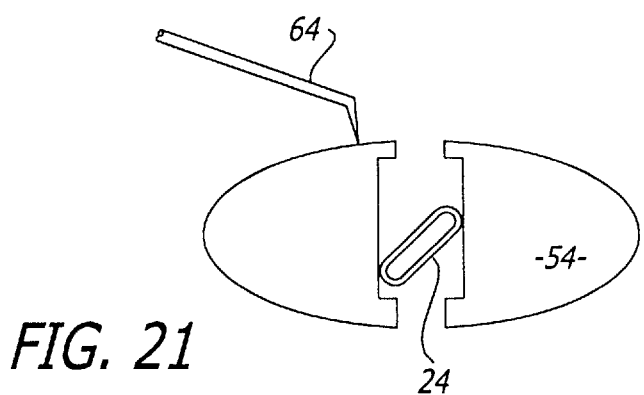
FIG. 21 is a schematic side view of FIG. 20.

FIGS. 19–21 show another procedure for cracking the lense 54. The tip 20 cuts a single groove 60 in the lense 54. While embedded in the lense 54, the distal end 24 is rotated from the vertical position to the horizontal position. The rotation of the tip 20 cracks the lense 54. The process of cutting grooves and cracking the lense 54 is repeated to create a plurality of lense fragments. The tip is rotated to the horizontal position and the lense fragments are then emulsified and aspirated by the system.

The present invention thus provides a flat phaco tip that is more efficient than tips of the prior art. The flat tip can be used to perform phaco procedures that are faster and have a higher margin of safety than procedures of the prior art.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A phaco emulsifying tip, comprising:

a tip which has an inner aspiration channel, said tip having a cylindrical proximal end and a flat distal end which has an oblong opening that provides fluid communication to said inner aspiration channel, said oblong opening of said flat distal end forms a pair of inner shoulders at said cylindrical proximal end that are within said inner aspiration channel and face said oblong opening to induce a cavitation of a fluid.

2. The tip as recited in claim 1, wherein said tip has a pair of outer shoulder areas located at said base of said flat distal end.

3. The tip as recited in claim 1, wherein said tip has an oblique cutting edge.

4. The tip as recited in claim 1, wherein said flat distal end has a width that is greater than a diameter of said cylindrical shaped proximal end.

5. The tip as recited in claim 1, further comprising an outer sleeve that is coupled to said tip and which has an irrigation port.

\* \* \* \* \*